United States Patent [19]  [11] 4,220,466
Patel  [45] Sep. 2, 1980

[54] 4,5-DICYANOIMIDAZOLES AND USE AS HERBICIDES

[75] Inventor: Natu R. Patel, Shawnee Mission, Kans.

[73] Assignee: Gulf Oil Corporation, Pittsburgh, Pa.

[21] Appl. No.: 628,003

[22] Filed: Nov. 3, 1975

[51] Int. Cl.³ .......................................... A01N 43/50
[52] U.S. Cl. ..................................... 71/92; 548/341; 548/337
[58] Field of Search ........................... 71/92; 260/309; 548/341, 337

[56] References Cited

U.S. PATENT DOCUMENTS

| | | | |
|---|---|---|---|
| 2,534,331 | 12/1950 | Woodward | 260/309 |
| 3,326,662 | 6/1967 | Toyosato et al. | 71/92 |
| 3,423,420 | 1/1969 | Buchel et al. | 260/309 |
| 3,501,286 | 3/1970 | Draber et al. | 71/92 |
| 3,806,517 | 4/1974 | Begland | 260/309 |
| 3,869,274 | 4/1975 | Corvetti et al. | 71/92 |

*Primary Examiner*—Catherine L. Mills
*Attorney, Agent, or Firm*—Carl A. Cline

[57] ABSTRACT

Unwanted vegetation is combated both pre- and post-emergently by application of various compounds having the general structural formula:

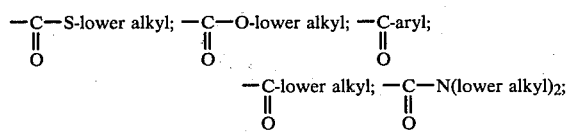

in which R is H, lower alkyl or cycloalkyl, lower alkoxy, phenyl or substituted phenyl and R' is one of the following: H;

$$-\underset{\underset{O}{\|}}{C}-\text{S-lower alkyl}; \quad -\underset{\underset{O}{\|}}{C}-\text{O-lower alkyl}; \quad -\underset{\underset{O}{\|}}{C}-\text{aryl};$$

$$-\underset{\underset{O}{\|}}{C}-\text{lower alkyl}; \quad -\underset{\underset{O}{\|}}{C}-\text{N(lower alkyl)}_2;$$

or phenylsulfonyl.

70 Claims, No Drawings

4,5-DICYANOIMIDAZOLES AND USE AS HERBICIDES

DESCRIPTION OF THE INVENTION

Background

In the United States there are now only five agricultural herbicides which account for about seventy percent of the entire herbicide market. Each of these herbicides belongs to a separate chemical class and each is used at the rate of more than ten million pounds per year. Other compounds of these same general chemical classes are also made and used, so that about eighty percent of the herbicides in use today belong to only five chemical classes. This situation has existed for more than a decade. A similar situation has also existed with respect to insecticides and has resulted in nearly disastrous development of insecticide-resistant strains of insects in some areas. The development of resistant strains of weeds occurs less readily than with insects because the existance of dormant seeds prevents the killing of almost all of the individuals of a single generation. The seeds which germinate during any given growing season inevitably are from several generations of plants. Nevertheless, continuous growing of the same crops and use of herbicides of the same chemical classes over the last two decades has had its effect. Strains of weeds are beginning to appear in some areas which are resistant to the best herbicides which are presently available. It is imperative that new chemical classes of herbicides be discovered and that various chemical types of herbicides be used in rotation, so as to prevent further development of resistant weeds. Otherwise it appears likely that within a few years each of the principal crops will be accompanied by weeds that have developed virtually the same selective herbicide resistance as the crop plants.

Summary

I have now discovered that a class of compounds having the general structural formula;

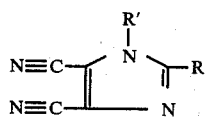

in which R is H, lower ($C_1$ to $C_5$) alkyl or cycloalkyl, lower ($C_1$ to $C_5$) alkoxy, phenyl or substituted phenyl and R' is one of the following; H,

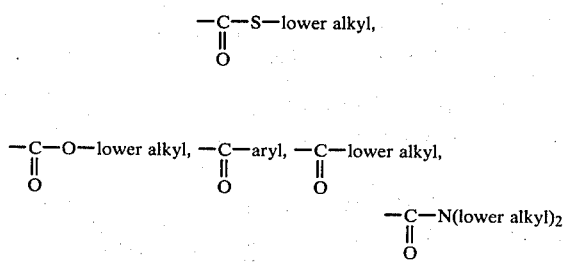

or phenylsulfonyl are useful as selective herbicides. Of this new class of herbicides, all except those in which R' is hydrogen are believed to be novel compounds.

Detailed Description

Since the new herbicides belong to a large class, it is impractical to exemplify all of the variations of substituents within the class. In the discussion which follows, however, illustrative examples are given of representative types of compounds and synthesis methods are presented so that a skilled worker in the art will have the information necessary for preparation of the other compounds of the class which are not specifically exemplified.

Synthesis of the Herbicides 4,5-Dicyanoimidazole, and 2-methyl and 2-ethyl 4,5-dicyanoimidazoles may be prepared according to the method disclosed in U.S. Pat. No. 2,534,331 (1950).

2-Isopropyl-4,5-dicyanoimidazole and 2-tert.butyl-4,5-dicyanoimidazole are obtained by the condensation of isobutyraldehyde and pivalaldehyde, respectively with diaminomaleonitrile to give Schiff's bases. The oxidative cyclization of these intermediates with lead tetraacetate then gave the corresponding dicyanoimidazoles TABLE 1, equation (1). Similarly lead tetraacetate oxidation of ethoxymethyleneiminoaminomaleonitrile gave 2-ethoxy-4,5-dicyanoimidazole. These compounds have also been prepared by routes disclosed in the following references:

R. W. Begland et al, J. Org. Chem., 39 2341 (1974);
R. W. Begland, U.S. Pat. No. 3,806,517 (1974).
F. J. Wiegert, U.S. Pat. No. 3,778,446 (1973).

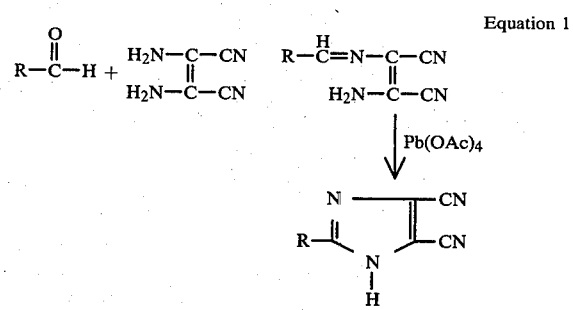

Equation 1

R = Branched alkyl group, aryl or substituted aryl group.

2-Alkyl- and 2-aryl-4,5-dicyanoimidazoles are allowed to react with the appropriate chlorothiolformate, chloroformate, acid chloride or sulfonyl chloride in acetone in the presence of a base at ice bath temperature to give the corresponding 1-acyl derivatives (equation 2). (TABLES II to V.)

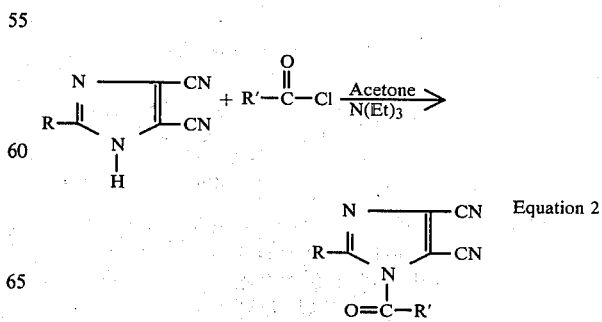

Equation 2

R' = —S—alkyl, —O—alkyl, aryl, alkyl.

Similarly the urea derivatives (TABLE V) were prepared by refluxing for 3 days in 1,4-dioxane.

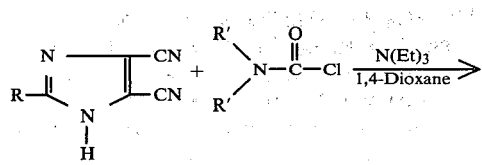

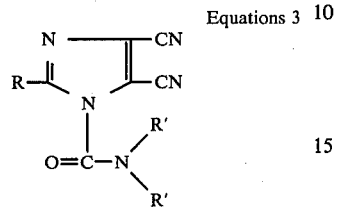

Equations 3

R' = —CH₃, —CH₂—CH₃.

Following are illustrative synthesis procedures.

Isobutylideneiminoaminomaleonitrile

To a stirred suspension of 10.8 g (0.1 mole) diaminomaleonitrile in 100 ml of absolute ethanol 7.2 g (0.1 mole) of distilled isobutyraldehyde is added dropwise. The mixture is stirred at room temperature overnight to give a clean solution. Evaporate to dryness and stir the residue in cold water. Filter, wash with water and dry to give 11.5 g, mp 83°–85° (71%) whitish product.

2-Isopropyl-4,5-dicyanoimidazole

To a stirred mixture of 9.2 g (0.05 mole) of isobutylideneiminoaminomaleonitrile in 100 ml of dry benzene at 5° C. under dry conditions lead tetraacetate 25 g (0.057 mole) is added in parts while keeping the temperature at approximately 10° C. Let it warm to room temperature and stir overnight. Cool the mixture to approximately 10° C., filter wash with benzene, dry and stir the residue in 100 ml water. The aqueous mixture is acidified to approximately pH 4 and extracted with ethyl acetate. Dry and evaporate to give 4.5 g, mp 146°–49°, (49%) product.

Methyl 4,5-dicyanoimidazole-1-thiolcarboxylate

To a stirred ice cold solution of 4.5 g (0.038 mole) 4,5-dicyanoimidazole, triethylamine 4.2 g (0.042 mole), and 4.7 g (0.042 mole) of methylchlorothiolformate are added dropwise in succession. Let it stir for 2 hours in ice bath and at room temperature overnight. The mixture is then poured into ice water and dried to give 6.0 g, mp 131°–33° (83%) product.

Analytical sample recrystallized from hexane: white flakes mp 132°–34°.

Anal. Calcd. for $C_7H_4N_4OS$; C, 43.74, H, 2.10; N, 29.15. Found: C, 43.36; H, 2.40; N, 29.41.

Methyl 2-methyl-4,5-dicyanoimidazole-1-carboxylate

Synthesis procedure and workup method are similar to those employed for the preparation of methyl 4,5-dicyanoimidazole-1-thiolcarboxylate.

White product m.p. 113°–15° (23%)

Anal. Calcd. for $C_8H_6N_4O_2$: C, 50.53; H, 3.18; N, 29.46. Found: C, 50.39; H, 3.39; N, 29.35.

1-(3'-Chlorobenzoyl)-2-methyl-4,5-dicyanoimidazole

Synthesis procedure and work up method are similar to those employed for the preparation of methyl 4,5-dicyanoimidazole-1-thiolcarboxylate.

Yellow product (74%). Recrystallization from benzene-hexane yields yellowish crystals, m.p. 141°–42°.

Anal. calcd. for $C_{13}H_7ClN_4O$: C, 57.69; H, 2.69; N, 20.70. Found: C, 57.62; H, 2.69; N, 20.96.

1-(N,N-Dimethylcarbamoyl)-4,5-dicyanoimidazole

To 50 ml of dry 1,4-dioxane 6.0 g (0.05 mole) of 4,5-dicyanoimidazole, 5.0 g (0.05 mole) of triethylamine and 6.0 g (0.055 mole) of dimethylcarbamoyl chloride are added in succession at room temperature. This mixture is stirred and refluxed for 3 days, cooled to room temperature and evaporated to dryness. The residue is stirred in 50 ml of ethyl acetate and 50 ml water. The organic layer is separated, washed, dried and evaporated to give 8 g. (85%) of white product.

Recrystallization from benzene-hexane yields white needles, m.p. 89°–90°.

COMBATING UNWANTED VEGETATION

The novel herbicides are effective when used both post- and pre-emergently. In commercial use the compounds are formulated as herbicidal compositions in combination with an inert diluent and a surface active agent. There is described below an illustrative procedure for herbicidal use of the compounds under controlled conditions in the greenhouse so as to obtain data on phytotoxic activity and selectivity.

1. Post Emergent Use

An aqueous dispersion of each active compound is prepared by combining 0.4 gram of the compound with about 4 ml of a solvent-emulsifier mixture (3 parts of a commercial polyoxyethylated vegetable oil emulsifier, 1 part xylene, 1 part kerosene) and then adding water, with stirring, to a final volume of 40 ml.

The species of plants on which each compound is to be tested are planted in 4-inch pots in a greenhouse. Ten to 18 days after emergence of the plants, three pots of each species are sprayed with an aqueous dispersion of the active compound prepared as described above, at a rate of 5 lb of active compound per acre and at a spary volume of 60 gallons per acre. Approximately 2 weeks after the spray application the plants are observed and the results rated according to the following schedule:

DEGREE OF EFFECT

0 = no effect
1 = slight effect (temporary injury)
2 = moderate effect (some permanent injury)
3 = severe effect (some plants died)
4 = maximum effect (all plants died)

The same rating schedule is employed to judge pre-emergent results obtained according to the procedure below.

2. Pre-emergent Use

A solution of each active compound is prepared by dissolving 290 mg of the compound to be tested in 200 ml of acetone. Disposable expanded polystyrene trays about 2½ inches deep and about 1 square foot in area are prepared and sprayed with the acetone solution at the rate of 10 lb of active chemical per acre of sprayed area and are then covered with about one-fourth inch of soil.

Twenty-one days after seeding and treatment the plants are examined and herbicidal effects are rated according to the above schedule.

Both post-emergent and pre-emergent results which have been obtained with the herbicides are set forth in the following tables.

TABLE 1

HERBICIDAL USE OF COMPOUNDS OF THE FORMULA $$\begin{array}{c} N \longrightarrow C(CN) \\ R \longrightarrow \| \quad \| \\ N \longrightarrow C(CN) \\ | \\ H \end{array}$$

| Example No. | R | m.p. or b.p. | Type | Digitaria sanguinalis Crabgrass | Celosia plumosa Coxcomb | Bromis inermis Brome | Setaria italica Millet | Medicago sativa Alfalfa | Avena sativa Oats | Raphanus satovis Radish | Beta vulgaris Sugarbeet |
|---|---|---|---|---|---|---|---|---|---|---|---|
| 1 | —H | m.p. 168°–71° | PRE | 1 | 4 | 1 | 1 | — | — | 4 | 4 |
|   |   |   | POST | — | — | — | 3 | 4 | 4 | 4 | 4 |
| 2 | —CH$_3$ | m.p. 224°–27° | PRE | 3 | 4 | 4 | 4 | — | — | 4 | 4 |
|   |   |   | POST | — | — | — | 4 | 4 | 3 | 4 | 4 |
| 3 | —CH$_2$CH$_3$ | m.p. 182°–84° | PRE | 4 | 4 | 4 | 4 | — | — | 3 | 4 |
|   |   |   | POST | — | — | — | 4 | 4 | 3 | 4 | 4 |
| 4 | —CH(CH$_3$)$_2$ | m.p. 146°–49° | PRE | 3 | 4 | 3 | 3 | — | — | 4 | 4 |
|   |   |   | POST | — | — | — | 4 | 4 | 3 | 4 | 4 |
| 5 | C(CH$_3$)$_3$ | m.p. 146°–48° | PRE | 3 | 4 | 4 | 4 | — | — | 4 | 4 |
|   |   |   | POST | — | — | — | 4 | 4 | 4 | 4 | 4 |
| 6 | C$_6$H$_5$ | m.p. 135°–37° | PRE | — | 2 | — | — | — | — | 3 | 3 |
|   |   |   | POST | — | — | — | 1 | 4 | 1 | 4 | 4 |
| 7 | C$_6$H$_4$Cl(m) | m.p. 223°–25° | PRE | — | 1 | 1 | 4 | — | — | 1 | 3 |
|   |   |   | POST | — | — | — | — | 1 | 1 | 3 | 4 |
| 8 | cyclopropyl | m.p. 182°–4° | PRE | 4 | 4 | 4 | 4 | — | — | 4 | 4 |
|   |   |   | POST | — | — | — | 4 | 4 | 4 | 4 | 4 |
| 9 | C$_2$H$_5$O | m.p. 85°–86° | PRE | 2 | 3 | 4 | 3 | — | — | 4 | 4 |
|   |   |   | POST | — | — | — | 1 | 4 | 3 | 4 | 4 |
|   |   |   | PRE |   |   |   |   |   |   |   |   |
|   |   |   | POST |   |   |   |   |   |   |   |   |
|   |   |   | PRE |   |   |   |   |   |   |   |   |
|   |   |   | POST |   |   |   |   |   |   |   |   |
|   |   |   | PRE |   |   |   |   |   |   |   |   |
|   |   |   | POST |   |   |   |   |   |   |   |   |

TABLE II

HERBICIDAL USE OF COMPOUNDS OF THE FORMULA $$\begin{array}{c} N \longrightarrow C(CN) \\ R \longrightarrow \| \quad \| \\ N \longrightarrow C(CN) \\ | \\ C\!-\!S\!-\!R' \\ \| \\ O \end{array}$$

| Ex. No. | R | R' | m.p. or b.p. | Type | Digitaria sanguinalis Crabgrass | Celosia plumosa Coxcomb | Bromis inermis Brome | Setaria italica Millet | Medicago sativa Alfalfa | Avena sativa Oats | Raphanus satovis Radish | Beta vulgaris Sugarbeet |
|---|---|---|---|---|---|---|---|---|---|---|---|---|
| 10 | —H | —CH$_3$ | m.p. 132°–34° | PRE | 2 | 3 | 1 | 1 | — | — | 2 | 4 |
|    |    |    |    | POST | — | — | — | — | 2 | 2 | 3 | 4 |
| 11 | —H | —CH$_2$CH$_3$ | m.p. 79°–80° | PRE | 4 | 4 | 4 | 4 | — | — | 4 | 4 |
|    |    |    |    | POST | — | — | — | 1 | 4 | 2 | 4 | 4 |
| 12 | —H | —C$_4$H$_9$(n) | b.p. 162°/ 0.15 mm | PRE | 2 | 3 | 1 | 1 | — | — | 1 | 4 |
|    |    |    |    | POST | — | — | — | 2 | 4 | 4 | 4 | 4 |
| 13 | —CH$_3$ | —CH$_3$ | m.p. 102°–103° | PRE | 4 | 4 | 4 | 4 | — | — | 4 | 4 |
|    |    |    |    | POST | — | — | — | 3 | 4 | 3 | 4 | 4 |
| 14 | —CH$_3$ | —CH$_2$CH$_3$ | m.p. 44°–45° | PRE | 4 | 4 | 3 | 2 | — | — | 4 | 4 |
|    |    |    |    | POST | — | — | — | 1 | 4 | 3 | 4 | 4 |
| 15 | —CH$_2$CH$_3$ | —CH$_3$ | m.p. 65°–67° | PRE | 2 | 4 | 1 | 1 | — | — | 2 | 4 |
|    |    |    |    | POST | — | — | — | 4 | 4 | 3 | 4 | 4 |
| 16 | —CH$_2$CH$_3$ | —CH$_2$CH$_3$ | m.p. 43°–44° | PRE | 3 | 3 | 1 | 2 | — | — | 2 | 4 |
|    |    |    |    | POST | — | — | — | 4 | 4 | 2 | 4 | 4 |
| 17 | —CH$_2$CH$_3$ | (CH$_2$)$_2$CH$_3$ | b.p. 141°–42°/ 0.1 mm | PRE | 3 | 3 | 1 | 1 | — | — | 2 | 4 |
|    |    |    |    | POST | — | — | — | 4 | 4 | 1 | 4 | 4 |
| 18 | —CH$_2$CH$_3$ | —CH—(CH$_3$)$_2$ | b.p. 147°–149°/ 0.15 mm | PRE | 2 | 3 | 2 | 2 | — | — | 3 | 4 |
|    |    |    |    | POST | — | — | — | 4 | 4 | 4 | 4 | 4 |
| 19 | —CH(CH$_3$)$_2$ | —CH$_3$ | m.p. 79°–80° | PRE | 4 | 4 | 4 | 4 | — | — | — | — |
|    |    |    |    | POST | — | — | — | 1 | 4 | 2 | 4 | 4 |
| 20 | —CH(CH$_3$)$_2$ | —CH$_2$CH$_3$ | b.p. 138°–40°/ 0.2 mm | PRE | 2 | 3 | 1 | 3 | — | — | 4 | 4 |
|    |    |    |    | POST | — | — | — | 3 | 4 | 3 | 4 | 4 |
| 21 | C$_6$H$_5$ | —CH$_3$ | m.p. 108°–10° | PRE | — | 2 | — | — | — | — | 3 | 3 |
|    |    |    |    | POST | — | — | — | 2 | 4 | 1 | 4 | 4 |

TABLE II-continued
HERBICIDAL USE OF COMPOUNDS OF THE FORMULA $$\underset{\underset{O}{\overset{\|}{C-S-R'}}}{\underset{|}{N}} \underset{N}{\overset{}{\underset{}{\overset{}{\underset{}{R}}}}} \overset{CN}{\underset{CN}{}}$$

| Ex. No. | R | R' | m.p. or b.p. | Type | Digitaria sanguinalis Crab-grass | Celosia plumosa Coxcomb | Bromis inermis Brome | Setaria italica Millet | Medicago sativa Alfalfa | Avena sativa Oats | Raphanus sativovis Radish | Beta vulgaris Sugar-beet |
|---|---|---|---|---|---|---|---|---|---|---|---|---|
| 22 | —C$_6$H$_5$ | —CH$_2$CH$_3$ | m.p. 83°–85° | PRE | 1 | 2 | — | — | — | — | 3 | 4 |
|  |  |  |  | POST | — | — | — | 1 | 4 | 1 | 4 | 4 |
| 23 | (CH$_3$)$_2$CH— | —CH$_3$ | m.p. 79°–80° | PRE | 4 | 4 | 4 | 4 | — | — | 4 | 4 |
|  |  |  |  | POST | — | — | — | 1 | 4 | 2 | 4 | 4 |
| 24 | cyclopropyl | —CH$_3$ | m.p. 100°–102° | PRE | 4 | 4 | 4 | 4 | — | — | 4 | 4 |
|  |  |  |  | POST | — | — | — | 4 | 4 | 4 | 4 | 4 |
| 25 | (CH$_3$)$_2$CH— | CH$_3$CH$_2$CH$_2$— | b.p. 141°–2°/ 0.1 mm | PRE | 1 | 4 | 4 | 2 | — | — | 4 | 4 |
|  |  |  |  | POST | — | — | — | 3 | 4 | 3 | 4 | 4 |
| 26 | cyclopropyl | CH$_3$CH$_2$— | 63° | PRE | 4 | 4 | 4 | 4 | — | — | 4 | 4 |
|  |  |  |  | POST | — | — | — | 4 | 4 | 4 | 4 | 4 |
| 27 | cyclopropyl | CH$_3$CH$_2$CH$_2$— | b.p. 170°/ 0.1 mm | PRE | 3 | 4 | 4 | 4 | — | — | 4 | 4 |
|  |  |  |  | POST | — | — | — | 4 | 4 | 4 | 4 | 4 |
| 28 | C$_2$H$_5$O | —CH$_3$ | m.p. 141°–143° | PRE | 3 | 3 | 4 | 2 | — | — | 4 | 4 |
|  |  |  |  | POST | — | — | — | 1 | 4 | 2 | 4 | 4 |
| 29 | C$_2$H$_5$O | C$_2$H$_5$ | m.p. 101°–103° | PRE | 2 | 4 | 4 | 1 | — | — | 4 | 4 |
|  |  |  |  | POST | — | — | — | 3 | 4 | 3 | 4 | 4 |
|  |  |  |  | PRE |  |  |  |  |  |  |  |  |
|  |  |  |  | POST |  |  |  |  |  |  |  |  |
|  |  |  |  | PRE |  |  |  |  |  |  |  |  |
|  |  |  |  | POST |  |  |  |  |  |  |  |  |
|  |  |  |  | PRE |  |  |  |  |  |  |  |  |
|  |  |  |  | POST |  |  |  |  |  |  |  |  |
|  |  |  |  | PRE |  |  |  |  |  |  |  |  |
|  |  |  |  | POST |  |  |  |  |  |  |  |  |

TABLE III
HERBICIDAL USE OF COMPOUNDS OF THE FORMULA $$\underset{\underset{O}{\overset{\|}{C-O-R'}}}{\underset{|}{N}} \underset{N}{\overset{}{\underset{}{\overset{}{\underset{}{R}}}}} \overset{CN}{\underset{CN}{}}$$

| Ex. No. | R | R' | m.p. or b.p.(°C.) | Type | Digitaria sanguinalis Crab-grass | Celosia plumosa Coxcomb | Bromis inermis Brome | Setaria italica Millet | Medicago sativa Alfalfa | Avena sativa Oats | Raphanus satovis Radish | Beta vulgaris Sugar-beet |
|---|---|---|---|---|---|---|---|---|---|---|---|---|
| 30 | —CH$_3$ | —CH$_3$ | m.p. 113°–15° | PRE | 2 | 4 | 1 | 2 | — | — | 4 | 4 |
|  |  |  |  | POST | — | — | — | 2 | 4 | 3 | 4 | 4 |
| 31 | —CH$_2$CH$_3$ | —CH$_3$ | m.p. 68°–70° | PRE | 1 | 3 | 1 | 1 | — | — | 1 | 4 |
|  |  |  |  | POST | — | — | — | 4 | 4 | 2 | 4 | 4 |
| 32 | —CH$_2$CH$_3$ | —CH$_2$CH$_3$ | b.p. 160°/ 0.1 mm | PRE | 2 | 3 | 1 | 2 | — | — | 2 | 4 |
|  |  |  |  | POST | — | — | — | 4 | 4 | 3 | 4 | 4 |
| 33 | (CH$_3$)$_2$CH— | CH$_3$ | m.p. 72°–74° | PRE | 2 | 2 | 4 | 2 | — | — | 4 | 4 |
|  |  |  |  | POST | — | — | — | 4 | 4 | 4 | 4 | 4 |
| 34 | H | CH$_3$ | m.p. 51°–53° | PRE | 1 | 4 | 2 | 1 | — | — | 2 | 4 |
|  |  |  |  | POST | — | — | — | 1 | 3 | 4 | 4 | 4 |

TABLE IV

HERBICIDAL USE OF COMPOUNDS OF THE FORMULA

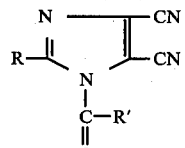

| Ex. No. | R | R' | m.p. or b.p. | Type | Digitaria sanguiosa Crabgrass | Celosia plumosa Coxcomb | Bromis inermis Brome | Setaria italica Millet | Medicago sativa Alfalfa | Avena sativa Oats | Raphanus sativa Radish | vulgaris satovis | Beta Sugarbeet |
|---|---|---|---|---|---|---|---|---|---|---|---|---|---|
| 35 | —CH₃ | —C₆H₅ | m.p. 102°–104° | PRE | 2 | 4 | 1 | 1 | — | — | 2 | 4 | |
|    |      |       |                | POST | — | — | — | 3 | 4 | 2 | 4 | 4 | |
| 36 | —CH₃ | —C₆H₅Cl(m) | m.p. 141°–42° | PRE | 1 | 4 | 1 | 1 | — | — | 2 | 4 | |
|    |      |            |               | POST | — | — | — | 3 | 4 | 2 | 4 | 4 | |
| 37 | —CH₂CH₃ | —C₆H₅ | m.p. 120°–22° | PRE | 3 | 3 | 4 | 3 | — | — | 4 | 4 | |
|    |         |       |               | POST | — | — | — | 2 | 4 | 1 | 2 | 4 | |
| 38 | —CH₂CH₃ | —C₆H₄Cl(m) | m.p. 105°–107° | PRE | 3 | 3 | 1 | 2 | — | — | 3 | 4 | |
|    |         |            |                | POST | — | — | — | 4 | 4 | 2 | 4 | 4 | |
| 39 | cyclopropyl | CH₃CH₂— | m.p. 56°–57° | PRE | 4 | 4 | 4 | 4 | — | — | 4 | 4 | |
|    |             |         |              | POST | — | — | — | 2 | 4 | 4 | 4 | 4 | |
| 40 | CH₃ | CH₃CH₂— | m.p. 119°–120° | PRE | 4 | 4 | 4 | 4 | — | — | 4 | 4 | |
|    |     |         |                | POST | — | — | — | 1 | 4 | 3 | 3 | 4 | |
| 41 | CH₃CH₂ | CH₃CH₂ | m.p. 64°–69° | PRE | 2 | 4 | 2 | 1 | — | — | 4 | 4 | |
|    |        |        |              | POST | — | — | — | 1 | 4 | 2 | 4 | 4 | |

TABLE V

HERBICIDAL USE OF COMPOUNDS OF THE FORMULA

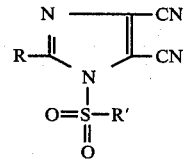

| Example No. | R | R' | m.p. or b.p. | Type | Digitaria sanguinalis Crabgrass | Celosia plumosa Coxcomb | Bromis inermis Brome | Setaria italica Millet | Medicago sativa Alfalfa | Avena sativa Oats | Raphanus satovis Radish | Beta vulgaris Sugarbeet |
|---|---|---|---|---|---|---|---|---|---|---|---|---|
| 42 | —CH₃ | —C₆H₅ | m.p. 138°–40° | PRE | 1 | 4 | 1 | 1 | — | — | 1 | 4 |
|    |      |       |               | POST | — | — | — | 4 | 4 | 1 | 3 | 4 |

TABLE VI

HERBICIDAL USE OF COMPOUNDS OF THE FORMULA

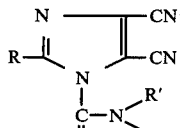

| Ex. No. | R | R' | m.p. or b.p. | Type | Digitaria Sanguinalis Crabgrass | Celosia plumosa Coxcomb | Bromis inermis Brome | Setaria italica Millet | Medicago sativa Alfalfa | Avena sativa Oats | Raphanus satovis Radish/beet | Beta vulgaris Sugarbeet |
|---|---|---|---|---|---|---|---|---|---|---|---|---|
| 43 | —H | —CH₃ | m.p. 89°–90° | PRE | 1 | 3 | 1 | 1 | — | — | 2 | 4 |
|    |    |      |              | POST | — | — | — | 2 | 4 | 2 | 4 | 4 |
| 44 | —H | —CH₂CH₃ | m.p. 118°–21° | PRE | 1 | 3 | 1 | 1 | — | — | 2 | 3 |
|    |    |         |               | POST | — | — | — | 2 | 4 | 1 | 4 | 4 |
| 45 | CH₃ | —CH₃ | m.p. 90°–91° | PRE | 1 | 2 | 1 | 2 | — | — | 2 | 4 |
|    |     |      |              | POST | — | — | — | 3 | 4 | 3 | 3 | 4 |
| 46 | —CH₂CH₃ | —CH₃ | b.p. 145°–46°/0.15 mm | PRE | 1 | 4 | 1 | 1 | — | — | 2 | 4 |
|    |         |      |                        | POST | — | — | — | 3 | 4 | 1 | 2 | 4 |
| 47 | —CH₂CH₃ | —CH₂CH₃ | b.p. 189°–90°/0.2 mm | PRE | — | 2 | 1 | 1 | — | — | 1 | 4 |
|    |         |         |                       | POST | — | — | — | 3 | 4 | 1 | 3 | 4 |
| 48 | (CH₃)₂CH— | CH₃ | m.p. 72°–74° | PRE | 0 | 1 | 3 | 1 | — | — | 3 | 4 |
|    |           |     |              | POST | — | — | — | 2 | 4 | 2 | 4 | 4 |
| 49 | cyclopropyl | CH₃ | m.p. 120°–123° | PRE | 2 | 4 | 4 | 1 | — | — | 4 | 4 |

TABLE VI-continued

HERBICIDAL USE OF COMPOUNDS OF THE FORMULA $$\begin{array}{c} N \equiv\!\!\!= C\!-\!CN \\ R\!-\!C\!\!=\!\!C\!-\!CN \\ | \\ N \\ | \\ C\!-\!N(R')_2 \\ \| \\ O \end{array}$$

| Ex. No. | R | R' | m.p. or b.p. | Type | Digitaria Sanguinalis Crab-grass | Celosia plumosa Cox-comb | Bromis inermis Brome | Setaria italica Millet | Medicago sativa Alfalfa | Avena sativa Oats | Raphanus satovis Radish/beet | Beta vulgaris Sugar- |
|---|---|---|---|---|---|---|---|---|---|---|---|---|
| | | | | POST | — | — | — | 0 | 4 | 1 | 4 | 4 |

To further illustrate the properties of the herbicides of this invention, there are presented in the following tables the results of herbicidal use of two specific compounds according to the procedures described above on a larger number of species and at various low rates of application. These two compounds have proved to be particularly useful for post-emergent control of weeds in such crops as corn, peanuts and soybeans, either alone or in combination with other herbicides.

TABLE VII

HERBICIDAL USE ON 24 SPECIES $$\begin{array}{c} CH_3 \\ \diagdown \\ HC\!-\!C\!=\!N\!-\!C\!-\!CN \\ \diagup \qquad \| \quad \| \\ CH_3 \quad N \quad C\!-\!CN \\ | \\ C\!-\!S\!-\!CH_2CH_3 \\ \| \\ O \end{array}$$
(No. 20)

$$\begin{array}{c} N\!-\!C\!-\!CN \\ \| \quad \| \\ CH_3CH_2\!-\!C \quad C\!-\!CN \\ | \\ N \\ | \\ C\!-\!S\!-\!CH_3 \\ \| \\ O \end{array}$$
(No. 15)

| | (No. 20) PRE | | (No. 20) POST | | (No. 15) PRE | | (No. 15) POST | |
|---|---|---|---|---|---|---|---|---|
| PLANT SPECIES | 3 lb/A | 1 lb/A | 3 lb/A | 1 lb/A | 3 lb/A | 1 lb/A | 3 lb/A | 1 lb/A |
| *Xanthium pensylvanicum* Cocklebur | 0 | 0 | 4 | 2 | 0 | 0 | 4 | 4 |
| *Chenopodium album* Lambsquarters | 1 | 0 | 4 | 3 | 1 | 1 | 4 | 4 |
| *Ipomea purpurea* Morning glory | 0 | 0 | 4 | 3 | 0 | 0 | 4 | 3 |
| *Amaranthus retroflexus* Pigweed | 1 | 0 | 2 | 2 | 1 | 1 | 4 | 4 |
| *Polygonum convolvulus* Wild Buckwheat | 0 | 0 | 4 | 4 | 0 | 0 | 4 | 4 |
| *Brassica kaber* Wild Mustard | 0 | 0 | 4 | 2 | 0 | 0 | 4 | 2 |
| *Echinochloa crusgalli* Barnyard grass | 0 | 0 | 1 | 0 | 0 | 0 | 2 | 1 |
| *Digitaria sanguinalis* Crabgrass | 0 | 0 | 1 | 0 | 0 | 0 | 2 | 1 |
| *Bromus tectorum* Downy Brome | 0 | 0 | 1 | 0 | 0 | 0 | 1 | 0 |
| *Setaria faberii* Giant Foxtail | 0 | 0 | 2 | 0 | 0 | 0 | 3 | 1 |
| *Setaria viridis* Green Foxtail | 0 | 0 | 2 | 0 | 0 | 0 | 4 | 4 |
| *Cuperus esculentis* Nutsedge | 0 | 0 | 0 | 0 | 0 | 0 | 0 | 0 |
| *Sorghum bicolor* Shatter Cane | 0 | 0 | 0 | 0 | 0 | 0 | 4 | 0 |
| *Avena fatua* Wild Oats | 0 | 0 | 2 | 0 | 0 | 0 | 1 | 0 |
| *Medicago sativa* Alfalfa | 0 | 0 | 4 | 1 | 1 | 0 | 4 | 4 |
| *Gossypium herbaceum* Cotton | 0 | 0 | 4 | 3 | 0 | 0 | 4 | 3 |
| *Arachis hypogaea* Peanut | 0 | 0 | 1 | 1 | 0 | 0 | 2 | 1 |
| *Soja max* Soybean | 0 | 0 | 4 | 1 | 0 | 0 | 3 | 1 |
| *Beta vulgaris* Sugar Beets | 0 | 0 | 4 | 4 | 0 | 0 | 4 | 4 |
| *Lycopersicum esculentum* Tomato | 0 | 0 | 4 | 4 | 0 | 0 | 4 | 4 |
| *Zea mays* Corn | 0 | 0 | 0 | 0 | 0 | 0 | 1 | 0 |
| *Sorghum vulgare* | | | | | | | | |

TABLE VII-continued
HERBICIDAL USE ON 24 SPECIES

| | (No. 20) | | | | (No. 15) | | | |
|---|---|---|---|---|---|---|---|---|
| | PRE | | POST | | PRE | | POST | |
| PLANT SPECIES | 3 lb/A | 1 lb/A | 3 lb/A | 1 lb/A | 3 lb/A | 1 lb/A | 3 lb/A | 1 lb/A |
| Grain Sorghum | 0 | 0 | 0 | 0 | 0 | 0 | 2 | 0 |
| *Oryza sativa* Rice | 0 | 0 | 2 | 1 | 0 | 0 | 2 | 1 |
| *Triticum aestivum* Wheat | 0 | 0 | 2 | 0 | 0 | 0 | 2 | 0 |

TABLE VIII
POST-EMERGENCE USE AT LOW RATES OF APPLICATION
PLANT SPECIES

| Compound No. | Rate lb/A | Pigweed | Alfalfa | Tomato | Cotton | Soybean | Peanut | Velvet leaf | Smart weed | Jimson weed | Sickle pod | Morning glory | Cocklebur |
|---|---|---|---|---|---|---|---|---|---|---|---|---|---|
| 15 | 2 | 4 | 4 | 4 | 4 | 3 | 1 | 4 | 4 | 4 | 4 | 4 | 4 |
|  | 1 | 4 | 3 | 4 | 4 | 2 | 0 | 4 | 4 | 4 | — | 4 | 4 |
|  | ½ | 3 | 3 | 3 | 3 | 1 | 0 | 4 | 3 | 4 | — | 3 | 4 |
|  | ¼ | 3 | 3 | 4 | 2 | 1 | 0 | 4 | 4 | 4 | — | 3 | 4 |
| 20 | 2 | 4 | 4 | 4 | 4 | 3 | 1 | 4 | 4 | 4 | 4 | 4 | 4 |
|  | 1 | 4 | 3 | 4 | 2 | 1 | 0 | 4 | 4 | 4 | 4 | 4 | 4 |
|  | ½ | 2 | 3 | 1 | 3 | 1 | 0 | 4 | 4 | 4 | 2 | 3 | 4 |
|  | ¼ | 3 | 3 | 4 | 2 | 1 | 0 | 4 | 4 | 4 | — | 2 | 3 |

I claim:

1. The method of combating unwanted vegetation comprising applying pre- or post-emergently an effective amount of a compound having the general structural formula:

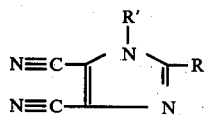

in which R is H and R' is —CO—S—CH₃.

2. The method of combating unwanted vegetation comprising applying pre- or post-emergently an effective amount of a compound having the general structural formula:

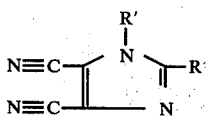

in which R is H and R' is —CO—S—CH₂CH₃.

3. The method of combating unwanted vegetation comprising applying pre- or post-emergently an effective amount of a compound having the general structural formula:

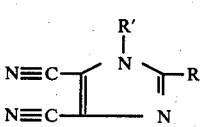

in which R is H and R' is —CO—S—(CH₂)₃CH₃.

4. The method of combating unwanted vegetation comprising applying pre- or post-emergently an effective amount of a compound having the general structural formula:

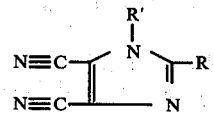

in which R is —CH₃ and R' is —CO—S—CH₃.

5. The method of combating unwanted vegetation comprising applying pre- or post-emergently an effective amount of a compound having the general structural formula:

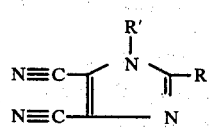

in which R is CH₃ and R' is —CO—S—CH₂CH₃.

6. The method of combating unwanted vegetation comprising applying pre- or post-emergently an effective amount of a compound having the general structural formula:

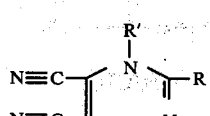

in which R is —CH₂CH₃ and R' is —CO—S—CH₃.

7. The method of combating unwanted vegetation comprising applying pre- or post-emergently an effective amount of a compound having the general structural formula:

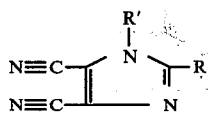

in which R is —CH₂CH₃ and R' is —CO—S—CH₂CH₃.

8. The method of combating unwanted vegetation comprising applying pre- or post-emergently an effective amount of a compound having the general structural formula:

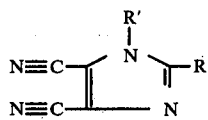

in which R is —CH₂CH₃ and R' is —CO—S—(CH₂)₂CH₃.

9. The method of combating unwanted vegetation comprising applying pre- or post-emergently an effective amount of a compound having the general structural formula:

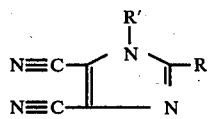

in which R is —CH₂CH₃ and R' is —CO—S—CH(CH₃)₂.

10. The method of combating unwanted vegetation comprising applying pre- or post-emergently an effective amount of a compound having the general structural formula:

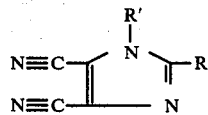

in which R is —CH(CH₃)₂ and R' is —CO—S—CH₃.

11. The method of combating unwanted vegetation comprising applying pre- or post-emergently an effective amount of a compound having the general structural formula:

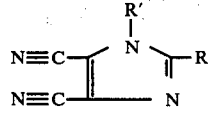

in which R is —CH(CH₃)₂ and R' is —CO—S—CH₂CH₃.

12. The method of combating unwanted vegetation comprising applying pre- or post-emergently an effective amount of a compound having the general structural formula:

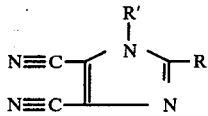

in which R is phenyl and R' is —CO—S—CH₃.

13. The method of combating unwanted vegetation comprising applying pre- or post-emergently an effective amount of a compound having the general structural formula:

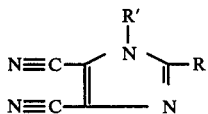

in which R is phenyl and R' is —CO—S—CH₂CH₃.

14. The method of combating unwanted vegetation comprising applying pre- or post-emergently an effective amount of a compound having the general structural formula:

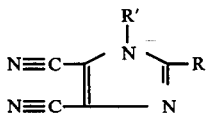

in which R is —CH(CH₃)₂ and R' is CO—S—CH₃.

15. The method of combating unwanted vegetation comprising applying pre- or post-emergently an effective amount of a compound having the general structural formula:

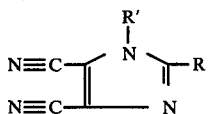

in which R is cyclopropyl and R' is —CO—S—CH₃.

16. The method of combating unwanted vegetation comprising applying pre- or post-emergently an effective amount of a compound having the general structural formula:

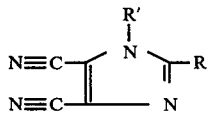

in which R is —CH(CH₃)₂ and R' is —CO—S—(CH₂)₂CH₃.

17. The method of combating unwanted vegetation comprising applying pre- or post-emergently an effective amount of a compound having the general structural formula:

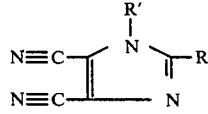

in which R is cyclopropyl and R' is —CO—S—CH₂CH₃.

18. The method of combating unwanted vegetation comprising applying pre- or post-emergently an effective amount of a compound having the general structural formula:

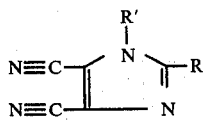

in which R is cyclopropyl and R' is —CO—S—(CH$_2$)$_2$CH$_3$.

19. The method of combating unwanted vegetation comprising applying pre- or post-emergently an effective amount of a compound having the general structural formula:

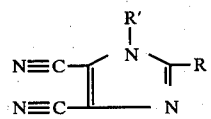

in which R is —OC$_2$H$_5$ and R' is —CO—S—CH$_3$.

20. The method of combating unwanted vegetation comprising applying pre- or post-emergently an effective amount of a compound having the general structural formula:

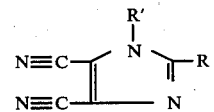

in which R is —OC$_2$H$_5$ and R' is —CO—S—CH$_2$CH$_3$.

21. The method of combating unwanted vegetation comprising applying pre- or post-emergently an effective amount of a compound having the general structural formula:

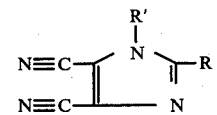

in which R is —CH$_3$ and R' is —COO—CH$_3$.

22. The method of combating unwanted vegetation comprising applying pre- or post-emergently an effective amount of a compound having the general structural formula:

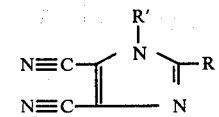

in which R is —CH$_2$CH$_3$ and R' is —COO—CH$_3$.

23. The method of combating unwanted vegetation comprising applying pre- or post-emergently an effective amount of a compound having the general structural formula:

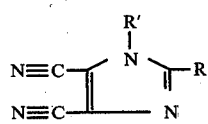

in which R is —CH$_2$CH$_3$ and R' is —COO—CH$_2$CH$_3$.

24. The method of combating unwanted vegetation comprising applying pre- or post-emergently an effective amount of a compound having the general structural formula:

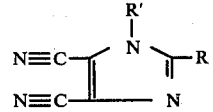

in which R is —CH(CH$_3$)$_2$ and R' is —COO—CH$_3$.

25. The method of combating unwanted vegetation comprising applying pre- or post-emergently an effective amount of a compound having the general structural formula:

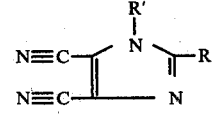

in which R is H and R' is —CO—O—CH$_3$.

26. The method of combating unwanted vegetation comprising applying pre- or post-emergently an effective amount of a compound having the general structural formula:

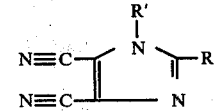

in which R is cyclopropyl and R' is —CO—CH$_2$CH$_3$.

27. The method of combating unwanted vegetation comprising applying pre- or post-emergently an effective amount of a compound having the general structural formula:

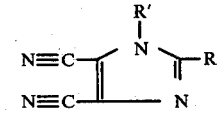

in which R is —CH$_3$ and R' is —CO—CH$_2$CH$_3$.

28. The method of combating unwanted vegetation comprising applying pre- or post-emergently an effective amount of a compound having the general structural formula:

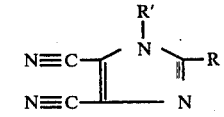

in which R is —CH$_2$CH$_3$ and R' is —CO—CH$_2$CH$_3$.

29. The method of combating unwanted vegetation comprising applying pre- or post-emergently an effective amount of a compound having the general structural formula:

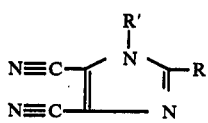

in which R is —H and R' is —CO—N(CH₃)₂.

30. The method of combating unwanted vegetation comprising applying pre- or post-emergently an effective amount of a compound having the general structural formula:

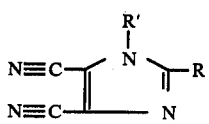

in which R is H and R' is —C0—N(CH₂CH₃)₂.

31. The method of combating unwanted vegetation comprising applying pre- or post-emergently an effective amount of a compound having the general structural formula:

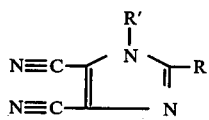

in which R is —CH₃ and R' is —CO—N(CH₃)₂.

32. The method of combating unwanted vegetation comprising applying pre- or post-emergently an effective amount of a compound having the general structural formula:

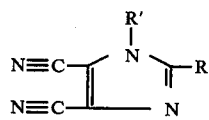

in which R is —CH₃CH₃ and R' is —CO—N(CH₃)₂.

33. The method of combating unwanted vegetation comprising applying pre- or post-emergently an effective amount of a compound having the general structural formula:

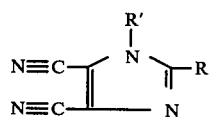

in which R is —CH₂CH₃ and R' is —CO—N(CH₂CH₃)₂.

34. The method of combating unwanted vegetation comprising applying pre- or post-emergently an effective amount of a compound having the general structural formula:

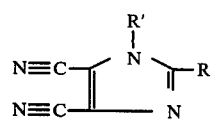

in which R is —CH(CH₃)₂ and R' is —CO—N(CH₃)₂.

35. The method of combating unwanted vegetation comprising applying pre- or post-emergently an effective amount of a compound having the general structural formula:

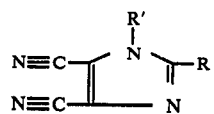

in which R is cyclopropyl and R' is —CON(CH₃)₂.

36. The herbicidal composition comprising the compound having the structural formula:

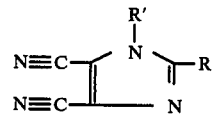

in which R is H and R' is —CO—S—CH₃ in combination with an inert diluent and a surface active agent.

37. The herbicidal composition comprising the compound having the structural formula:

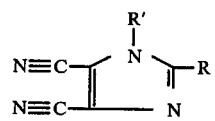

in which R is H and R' is —CO—S—CH₂CH₃ in combination with an inert diluent and a surface active agent.

38. The herbicidal composition comprising the compound having the structural formula:

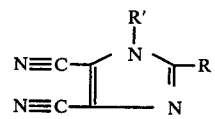

in which R is H and R' is —CO—S—(CH₂)₃CH₃ in combination with an inert diluent and a surface active agent.

39. The herbicidal composition comprising the compound having the structural formula:

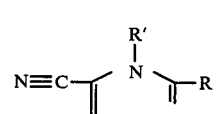

in which R is —CH₃ and R' is —CO—S—CH₃ in combination with an inert diluent and a surface active agent.

40. The herbicidal composition comprising the compound having the structural formula:

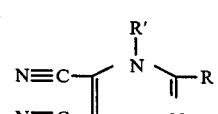

in which R is CH₃ and R' is —CO—S—CH₂CH₃ in combination with an inert diluent and a surface active agent.

41. The herbicidal composition comprising the compound having the structural formula:

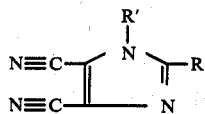

in which R is CH₂CH₃ and R' is —CO—S—CH₃ in combination with an inert diluent and a surface active agent.

42. The herbicidal composition comprising the compound having the structural formula:

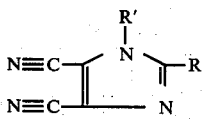

in which R is —CH₂CH₃ and R' is —CO—S—CH₂CH₃ in combination with an inert diluent and a surface active agent.

43. The herbicidal composition comprising the compound having the structural formula:

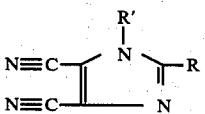

in which R is —CH₂CH₃ and R' is —CO—S—(CH₂)₂CH₃ in combination with an inert diluent and a surface active agent.

44. The herbicidal composition comprising the compound having the structural formula:

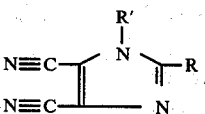

in which R is —CH₂CH₃ and R' is —CO—S—CH(CH₃)₂ in combination with an inert diluent and a surface active agent.

45. The herbicidal composition comprising the compound having the structural formula:

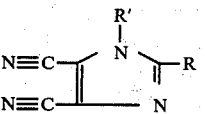

in which R is —CH(CH₃)₂ and R' is —CO—S—CH₃ in combination with an inert diluent and a surface active agent.

46. The herbicidal composition comprising the compound having the structural formula:

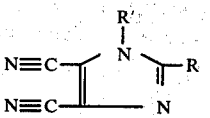

in which R is —CH(CH₃)₂ and R' is —CO—S—CH₂CH₃ in combination with an inert diluent and a surface active agent.

47. The herbicidal composition comprising the compound having the structural formula:

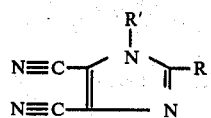

in which R is phenyl and R' is —CO—S—CH₃ in combination with an inert diluent and a surface active agent.

48. The herbicidal composition comprising the compound having the structural formula:

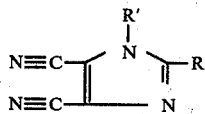

in which R is phenyl and R' is —CO—S—CH₂CH₃ in combination with an inert diluent and a surface active agent.

49. The herbicidal composition comprising the compound having the structural formula:

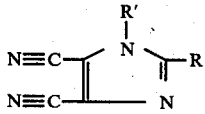

in which R is —CH(CH₃)₂ and R' is —CO—S—CH₃ in combination with an inert diluent and a surface active agent.

50. The herbicidal composition comprising the compound having the structural formula:

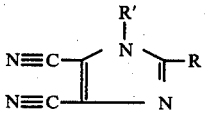

in which R is cyclopropyl and R' is —CO—S—CH₃ in combination with an inert diluent and a surface active agent.

51. The herbicidal composition comprising the compound having the structural formula:

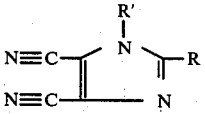

in which R is —CH(CH₃)₂ and R' is —CO—S—(CH₂)CH₃ in combination with an inert diluent and a surface active agent.

52. The herbicidal composition comprising the compound having the structural formula:

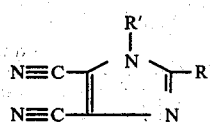

in which R is cyclopropyl and R' is —CO—S—CH₂CH₃ in combination with an inert diluent and a surface active agent.

53. The herbicidal composition comprising the compound having the structural formula:

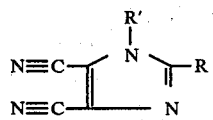

in which R is cyclopropyl and R' is —CO—S—(CH₂)₂CH₃ in combination with an inert diluent and a surface active agent.

54. The herbicidal composition comprising the compound having the structural formula:

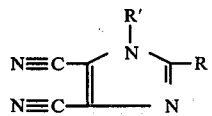

in which R is —OC₂H₅ and R' is —CO—S—CH₃ in combination with an inert diluent and a surface active agent.

55. The herbicidal composition comprising the compound having the structural formula:

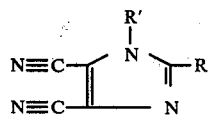

in which R is —OC₂H₅ and R' is —CO—S—CH₂CH₃ in combination with an inert diluent and a surface active agent.

56. The herbicidal composition comprising the compound having the structural formula:

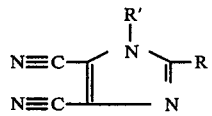

in which R is —CH₃ and R' is —CO—O—CH₃ in combination with an inert diluent and a surface active agent.

57. The herbicidal composition comprising the compound having the structural formula:

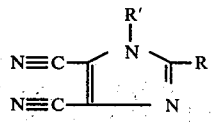

in which R is —CH₂CH₃ and R' is —CO—O—CH₃ in combination with an inert diluent and a surface active agent.

58. The herbicidal composition comprising the compound having the structural formula:

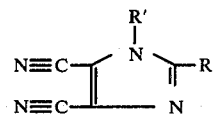

in which R is —CH₂CH₃ and R' is —CO—O—CH₂CH₃ in combination with an inert diluent and a surface active agent.

59. The herbicidal composition comprising the compound having the structural formula:

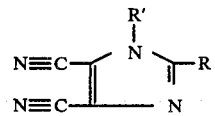

in which R is —CH(CH₃)₂ and R' is —CO—O—CH₃ in combination with an inert diluent and a surface active agent.

60. The herbicidal composition comprising the compound having the structural formula:

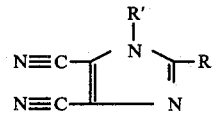

in which R is H and R' is —CO—O—CH₃ in combination with an inert diluent and a surface active agent.

61. The herbicidal composition comprising the compound having the structural formula:

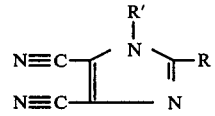

in which R is cyclopropyl and R' is —CO—CH₂CH₃ in combination with an inert diluent and a surface active agent.

62. The herbicidal composition comprising the compound having the structural formula:

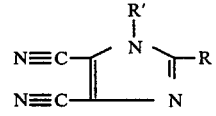

in which R is —CH₃ and R' is —CO—CH₂CH₃ in combination with an inert diluent and a surface active agent.

63. The herbicidal composition comprising the compound having the structural formula:

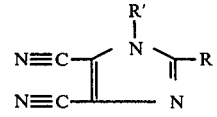

in which R is —CH₂CH₃ and R' is —CO—CH₂CH₃ in combination with an inert diluent and a surface active agent.

64. The herbicidal composition comprising the compound having the structural formula:

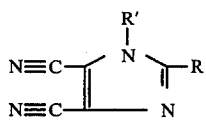

in which R is —H and R' is —CO—N—(CH₃)₂ in combination with an inert diluent and a surface active agent.

65. The herbicidal composition comprising the compound having the structural formula:

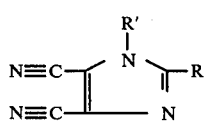

in which R is H and R' is —CO—N(CH₂CH₃)₂ in combination with an inert diluent and a surface active agent.

66. The herbicidal composition comprising the compound having the structural formula:

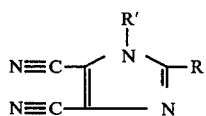

in which R is —CH₃ and R' is —CO—N(CH₃)₂ in combination with an inert diluent and a surface active agent.

67. The herbicidal composition comprising the compound having the structural formula:

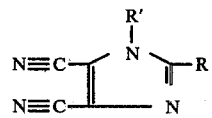

in which R is —CH₂CH₃ and R' is —CO—N(CH₃)₂ in combination with an inert diluent and a surface active agent.

68. The herbicidal composition comprising the compound having the structural formula:

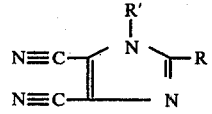

in which R is —CH₂CH₃ and R' is —CO—N(CH₂CH₃)₂ in combination with an inert diluent and a surface active agent.

69. The herbicidal composition comprising the compound having the structural formula:

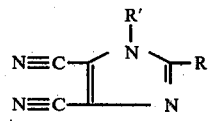

in which R is —CH(CH₃)₂ and R' is —CO—N(CH₃)₂ in combination with an inert diluent and a surface active agent.

70. The herbicidal composition comprising the compound having the structural formula:

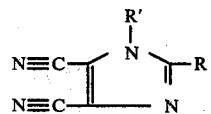

in which R is cyclopropyl and R' is —CON(CH₃)₂ in combination with an inert diluent and a surface active agent.

* * * * *

UNITED STATES PATENT OFFICE
CERTIFICATE OF CORRECTION

Patent No. 4,220,466　　　　　　　　　　Dated September 2, 1980

Inventor(s) Natu R. Patel

It is certified that error appears in the above-identified patent and that said Letters Patent are hereby corrected as shown below:

Column 7 and 8, Table II, Example No. 25, under the following headings should read----

| m.p. or b.p. | Type | Crab-grass | Cox-comb | Brome | Mil-let | Al-falfa | Oats | Rad-ish | Sugar-beet |
|---|---|---|---|---|---|---|---|---|---|
| b.p.141°-2°/ | PRE | 1 | 4 | 4 | 2 | - | - | 4 | 4 |
| 0.1 mm | POST | - | - | - | 3 | 4 | 3 | 4 | 4 |

Column 19, Claim 32, line 45, should read---- in which R is $-CH_2CH_3$ and R' is $-CO-N(CH_3)_2$. ----

Signed and Sealed this

*Sixth* Day of *January 1981*

[SEAL]

Attest:

SIDNEY A. DIAMOND

*Attesting Officer*　　　*Commissioner of Patents and Trademarks*